United States Patent [19]

Busse et al.

[11] Patent Number: 4,822,578

[45] Date of Patent: Apr. 18, 1989

[54] REMOVAL OF HYDROCARBON IMPURITIES FROM NATURAL GAS-DERIVED METHANE AND/OR ETHANE

[75] Inventors: Paul J. Busse; Douglas B. Taggart, both of Omaha, Nebr.

[73] Assignee: Quantum Chemical Corporation, Cincinnati, Ohio

[21] Appl. No.: 682,557

[22] Filed: Dec. 17, 1984

[51] Int. Cl.$^4$ .............................................. B01D 53/34
[52] U.S. Cl. .................... 423/245.3; 585/800; 585/868
[58] Field of Search ............... 423/245 R, 245 S; 585/800, 868; 502/347, 348

[56] References Cited

U.S. PATENT DOCUMENTS

| | | | |
|---|---|---|---|
| 1,908,312 | 5/1933 | Britton et al. | 585/800 |
| 2,381,707 | 8/1945 | Wood et al. | 423/245 S |
| 2,548,619 | 4/1951 | Ray | 585/800 |
| 3,317,278 | 5/1967 | Ruhemann et al. | 423/245 S |
| 4,328,382 | 5/1982 | Alter et al. | 585/844 |

FOREIGN PATENT DOCUMENTS

| | | | |
|---|---|---|---|
| 683515 | 3/1964 | Canada | 423/245 S |
| 8383 | 12/1973 | Netherlands | 423/245 S |
| 297842 | 8/1929 | United Kingdom . | |

OTHER PUBLICATIONS

*The Chemistry of Petroleum Hydrocarbons*, ed. by Brooks et al., Reinhold Publishing Corp. 1954, pp. 607-609.

*Primary Examiner*—John Doll
*Assistant Examiner*—Jeffrey Edwin Russel
*Attorney, Agent, or Firm*—Zarley, McKee, Thomte Voorhees & Sease

[57] ABSTRACT

A method is disclosed for the purification of methane and/or ethane which comprises oxidizing the higher hydrocarbon impurities in gas with oxygen at 175° C. to 375° C. in the presence of a catalyst which contains silver as the active component.

2 Claims, No Drawings

REMOVAL OF HYDROCARBON IMPURITIES FROM NATURAL GAS-DERIVED METHANE AND/OR ETHANE

BACKGROUND OF THE INVENTION

This invention describes a process for the removal or reduction in concentration of higher hydrocarbon impurities from methane and/or ethane. These impurities are typically found in methane that is derived from natural gas but may also be found in other gas mixtures. The higher hydrocarbon impurities are normally saturated aliphatics with from two to four carbon atoms. Thus, ethane, propane, butane, and isobutane are the predominant organic impurities in natural gas-derived methane. Higher hydrocarbons other than $C_4$ may also be present.

The $C_{2+}$ impurities are present in natural gas when it is removed from the ground together with inorganic contaminants such as nitrogen, hydrogen sulfide, carbon dioxide, and water. The inorganic components can be removed or reduced in concentration by a wide variety of chemical or physical procedures. The organic impurities can be and normally are separated from the natural gas for economic reasons. The $C_{2+}$ hydrocarbons have a greater economic value than does methane itself.

The heavier hydrocarbon components may be removed from the methane and/or ethane by either physical or chemical procedures. Physical procedures for hydrocarbon removal are represented by distillation and absorption. Both methods are based on equilibrium processes which require multiple steps for each additional increment of hydrocarbon removal. In addition, the physical methods generally are operated under cryogenic conditions which are comparatively costly. As a consequence, physical methods of separation are terminated at an economic barrier depending on the economic advantage of removing an additional increment of higher hydrocarbons or at the desired purity level which may be beyond the economic barrier. It is particularly costly to purify methane and/or ethane beyond the economic barrier.

An alternative to physical methods of hydrocarbon removal from methane is the use of catalytic reduction. In this process, excess hydrogen is mixed with the impure gas stream which is then fed to a catalytic reactor in which the higher hydrocarbons are converted to methane. This procedure does not extract the value of the hydrocarbons but does reduce their concentration. However, hydrogen is a relatively expensive material and is not always conveniently available.

In many cases the higher hydrocarbon content of methane and/or ethane does not affect its use and in some cases it may even be beneficial. However, in certain cases, such as the use of methane ballast in an ethylene oxide reactor, the ethane concentration must be controlled below certain levels and the complete absence of propane and higher hydrocarbons is preferred. To accomplish this control of the higher hydrocarbon concentration via the extant physical or chemical procedures would be complicated and expensive or both. Thus it can be seen that there is a need for a method which is capable of treating gas streams of methane and/or ethane containing relatively small amounts of higher hydrocarbons to reduce the concentration of higher hydrocarbons in methane and/or ethane to very low levels without the necessity of using the relatively expensive and sometimes unavailable hydrogen which is required in the commercially used catalytic processes.

SUMMARY OF THE INVENTION

The present invention provides a method of purification of methane, ethane or mixtures thereof which is based on oxidation of the higher hydrocarbon impurities in the gas. The oxidizing agent is oxygen and the process is conducted in a catalytic reactor operating in the temperature range of 175 to 375° C. Catalysts effective for this process contain silver as the active component.

The process consists of mixing a sufficient quantity of oxygen with the gas stream to permit combustion of the higher hydrocarbon contaminants. This stream is then passed through a catalyst bed providing the required conditions of oxidation. The resulting products of the purification step are carbon dioxide and water. These may be removed via conventional processes or left in the gas stream as desired.

DETAILED DESCRIPTION OF THE INVENTION

When an impure methane stream containing oxygen and optionally an inert gas such as nitrogen is passed over a catalyst as described below, combustion occurs predominantly in the order $C_4$ before $C_3$ before $C_2$ before $C_1$. With the catalysts described herein, the combustion process is normally very efficient providing carbon dioxide and water as the sole products. Control of the reaction can be achieved by controlling the variables of oxygen concentration, reactor temperature, and flow rate. By proper adjustment of these parameters, $C_{3+}$ hydrocarbons can be removed with little effect on ethane or methane concentration. The process can then be operated in a manner to significantly reduce the ethane concentration with relatively little reaction of methane. In some situations, the $C_{2+}$ hydrocarbons can be removed in one oxidizing step.

It goes without saying that for economic reasons it would be preferred to remove all of the higher hydrocarbons in a one-step process if that is possible. The process of the present invention can be performed in one step if the concentrations of the higher hydrocarbons are such that the oxygen concentration required to oxidize them is below the flammability limit of the gas mixtures so that the purification can take place without fear of an explosion. The methane and/or ethane stream and the oxygen pass into a catalytic reactor wherein the reaction temperature is controlled within the range of 175° to 375° C. If the temperature is below 175° C., then the reactivity is insufficient and if the temperature is above 375° C., then too much methane and/or ethane is oxidized. The oxygen concentration should be maintained at a level higher than but close to the stoichiometric concentration required to oxidize the higher hydrocarbons. Preferably, the oxygen concentration range is from 0.5% to 1% above the stoichiometric concentration because more oxygen provides no benefit and would bring the mix closer to the flammability limit.

The amount of time that the gas mixture is in contact with the catalyst is also an important variable. The contact time can be increased by increasing the size of the reactor. It can also be increased by slowing down the flow rate of the gases through the reactor. The contact time is generally measured in terms of space velocity in units of hour$^{-1}$. Thus, it is preferred that the space velocity be in the range from about 50 to about 1,000 hour$^{-1}$, preferably for the most practical operation 100 to about 500 hour$^{-1}$, if the reaction takes place at atmospheric pressure because it allows maximum use of the reactor. Higher flow rates can be used if the temperature is increased.

In situations where the concentration of the higher hydrocarbons requires an oxygen concentration which is above the flammability limit of the gas mixture, multiple oxidation steps are required. Preferably, two oxidations take place. In each oxidation step, the concentration of the oxygen is kept below the flammability limit because the oxygen concentration requres only that necessary to oxidize the higher hydrocarbons, $C_{3+}$, in the first step and, if it is to be removed, the ethane in the second step. This is possible because the oxidation occurs selectively with the higher hydrocarbons being oxidized before the lower hydrocarbons. The first oxidation removes almost all of the $C_{3+}$ hydrocarbons and the second removes as much of the ethane as is possible although it is very difficult to separate out all of the ethane without also oxidizing some methane.

The $C_{3+}$ hydrocarbons are oxidized by passing the methane and/or ethane stream over a silver catalyst at a temperature in the range of 175° C. to 375° C., preferably 230° C. to 320° C. The oxygen concentration should be maintained close to the stoichiometric concentration required for removal of the amount of $C_{3+}$ hydrocarbons present in the gas, preferably within 0.5 to 1% of this amount. The space velocity is also important here. In order to obtain optimum results, the space velocity should be kept in the range of 50 to 1,000 hour$^{-1}$, preferably for the most practical operation 100 to about 500 hour$^{-1}$.

If purified methane is desired, the ethane can be oxidized by passing the gas stream over a silver catalyst at a temperature in the range of 175° C. to 375° C., preferably 250° C. to 350° C. The oxygen concentration should be maintained close to the stoichiometric concentration required for removal of the amount of ethane present in the methane, preferably within 0.5 to 1% of this amount. The space velocity is again important. In order to obtain optimum results, the space velocity should be kept in the range of 50 to 1,000 hour$^{-1}$, preferably for the most practical operation 100 to about 500 hour$^{-1}$.

A wide variety of silver-based catalysts can be used to advantage in the present invention. These catalysts generally comprise a silver salt deposited on a porous support material such as alumina, silica or other inert refractory material. The catalyst might also include promoters such as alkali metals and alkaline earth metals. Commercially existing ethylene oxide silver-based catalysts generally provide acceptable performance in this process. Catalysts of this type are described in U.S. Pat. No. 3,725,307, issued Apr. 3, 1973.

The process may be operated with inert gases such as nitrogen or argon in the gas stream. The combustion products of the oxidation reaction are carbon dioxide and water and may be removed by conventional purification techniques if their presence is not desired in the purified methane stream. For use in an ethylene oxide reactor, the presence of carbon dioxide or water in the methane stream should not be detrimental to the process as both components are normally present in the reactor. If oxygen is not totally consumed in the purification process, the unreacted oxygen may be used to supplement the oxygen feed to the reactor.

The process is capable of reducing $C_{3+}$ concentrations to below gas chromatographic detection levels, to the 5 ppm level or less, with oxygen selectivities of 90% or more. It is also capable of reducing the ethane concentration of a methane stream to the 100 ppm level or less. The oxygen selectivity is defined as the percentage of oxygen consumed for removal of $C_{2+}$ hydrocarbons divided by the total oxygen consumed $$\text{Oxygen Selectivity} = 100 \times \frac{\text{Oxygen Consumed for } C_{2+}}{\text{Total Oxygen Consumed}}$$

Methane selectivity for this process when operated under preferred conditions is normally greater than 99%.

$$\text{Methane Selectivity} = 100 \times \frac{\text{Methane Output}}{\text{Methane Input}}$$

EXAMPLE I

Six samples of silver based catalysts were utilized for the evaluations reported herein. The test reactor in which the catalysts were evaluated consisted of ½ inch stainless steel tubes located in an oven with a preheating zone for the gas feed. The catalysts were evaluated under the conditions indicated in the tables and the products were evaluated by gas chromatography. In all of the following experiments, the catalyst was placed in the reactor and used to oxidize the indicated hydrocarbons at atmospheric pressure under the specified conditions.

Catalyst F was a sample of ethylene oxide catalyst that has been used in the manufacture of ethylene oxide. Catalysts A through E were prepared by impregnation with a mixture of a silver salt, one or more promoters as described below, lactic acid and water. The support used for all five catalysts was Norton SA-5202 which is a low surface area alumina support in the form of ¼ inch spheres. The impregnated support was dried at 60° C., and then activated via procedures designated in the table.

| | Catalyst Preparation and Activation | | | | |
|---|---|---|---|---|---|
| Catalyst | Silver Salt gm. | Barium Carbonate gm. | Sodium Carbonate gm. | Total Volume ml. | Activation Procedure |
| A | Carbonate 16.2 | .705 | — | 100 | 1, 2, 3 |
| B | Oxide 13.6 | .704 | .505 | 100 | 1 |
| C | Carbonate 16.2 | .700 | .506 | 100 | 1, 2, 3 |
| D | Oxide 13.6 | .704 | — | 100 | 1, 2, 3 |
| E | Oxide 13.6 | .300 | — | 100 | 1, 2 |

1 - under nitrogen for 5 to 6 hours.
2 - under 5% oxygen in nitrogen for 2 hours
3 - under 5% hydrogen in nitrogen for 2 hours

TABLE 1

| Catalyst | Temp. °C. | $C_{3+}$ Conc. ppm | $C_{3+}$ Conv. % | Oxygen Sel. % | Methane Sel. % | Flow Rate ml./min. |
|---|---|---|---|---|---|---|
| A | 265 | 239 | 94.7 | 80.3 | 99.9 | 70 |
| | 248 | 239 | 98.2 | 93.4 | 100.0 | 55 |
| | 243 | 239 | 100.0 | 92.3 | 99.9 | 40 |
| B | 284 | 239 | 67.4 | 59.3 | 99.9 | 55 |
| | 280 | 239 | 70.1 | 68.2 | 99.9 | 40 |

TABLE 1-continued

| Catalyst | Temp. °C. | $C_{3+}$ Conc. ppm | $C_{3+}$ Conv. % | Oxygen Sel. % | Methane Sel. % | Flow Rate ml./min. |
|---|---|---|---|---|---|---|
| C | 284 | 239 | 80.9 | 84.5 | 99.9 | 55 |
|   | 280 | 239 | 87.7 | 84.8 | 99.9 | 40 |
| D | 277 | 102 | 100.0 | 47.0 | 99.5 | 70 |
| E | 277 | 102 | 85.4 | 45.7 | 99.7 | 70 |
| F | 277 | 102 | 74.6 | 47.3 | 99.8 | 70 |

While all the catalysts performed properly, Catalysts A and C were particularly good at selectively converting the $C_{3+}$ hydrocarbons.

TABLE 2

| Catalyst | Temp. °C. | $C_2$ Conc. % | $C_2$ Conv. % | Oxygen Sel. % | Methane Sel. % | Flow Rate |
|---|---|---|---|---|---|---|
| A | 302 | .811 | 58.4 | 53.7 | 98.9 | 55 |
|   | 282 | .811 | 35.0 | 68.2 | 99.6 | 70 |
|   | 280 | .811 | 65.1 | 52.7 | 98.6 | 40 |
|   | 248 | .811 | 23.1 | 93.4 | 100.0 | 55 |
|   | 243 | .811 | 27.1 | 92.3 | 99.9 | 40 |
| B | 302 | .811 | 8.0 | 48.2 | 99.8 | 55 |
|   | 298 | .811 | 9.6 | 50.6 | 99.8 | 40 |
| C | 302 | .811 | 17.8 | 73.8 | 99.8 | 55 |
|   | 298 | .811 | 20.6 | 75.2 | 99.8 | 40 |
| D | 282 | .787 | 35.4 | 42.2 | 99.3 | 70 |
| E | 304 | .787 | 19.6 | 39.0 | 99.6 | 70 |
| F | 304 | .787 | 18.4 | 40.7 | 99.6 | 70 |

All of the catalysts worked reasonably well, but Catalysts A and C were the best at converting ethane.

TABLE 3

Experiments with High Concentrations of $C_{3+}$ Hydrocarbons Catalyst A

| Oxygen Conc. % | Temp. °C. | $C_{3+}$ Conc. % | $C_{3+}$ Conv. % | Oxygen Sel. % | Methane Sel. % | Flow Rate |
|---|---|---|---|---|---|---|
| 2 | 297 | .765 | 76.1 | 96.0 | 99.9 | 70 |
| 3 | 297 | .765 | 89.6 | 92.6 | 99.8 | 70 |

Catalyst A removed a high percentage of $C_{3+}$ hydrocarbons. Thus, a second pass could have easily removed the remaining hydrocarbons.

EXAMPLE II

Ethane may contain propane and butane as impurities which may be removed by oxidative purification. The reacted propane and butane is converted to carbon dioxide and water. The inorganic combustion products may be removed by conventional procedures if so desired.

If the oxygen concentration required for removal of the $C_{3+}$ hydrocarbons is higher than the flammability limit of the mixture, a two or more step process may be conducted in which oxygen is added to the ethane stream at a safe concentration. This mixture is fed to the catalytic reactor where oxidation of part of the $C_{3+}$ hydrocarbons is conducted. The partially purified ethane stream may again be treated with a second portion of oxygen and reacted again. This procedure may be repeated until the $C_{3+}$ concentration is reduced to the desired level.

An ethane stream containing 1,000 ppm of propane and 200 ppm of butane is mixed with oxygen to give an oxygen concentration of 1.25% in the gas mixture. The resulting mix is fed to the reactor containing the catalyst at a space velocity of 150 per hour and a temperature of 220°–230° C. The $C_{3+}$ concentration of the stream leaving the reactor is greatly reduced.

We claim:

1. A method for the purification of methane, ethane and mixtures thereof which comprises:
   (a) first oxidizing the $C_{3+}$ hydrocarbon impurities in the gas with oxygen at 175° C. to 375° C. in the presence of a catalyst which contains silver as the active component, and
   (b) then oxidizing the ethane in the gas with oxygen at 175° C. to 375° C. in the presence of a catalyst which contains silver as the active component.

2. The method of claim 1 wherein the oxygen concentration in each step is slightly in excess of the stoichiometric concentration required to oxidize all of the hydrocarbon impurities in the gas.

* * * * *